(12) United States Patent
Hubert et al.

(10) Patent No.: US 6,212,937 B1
(45) Date of Patent: Apr. 10, 2001

(54) STACK GAS EMISSIONS MONITORING SYSTEM

(75) Inventors: David J. Hubert; Brian R. Gardner, both of Jackson; Brian C. Pape, Essexville, all of MI (US)

(73) Assignee: Consumers Energy Company, Jackson, MI (US)

( * ) Notice: Subject to any disclaimer, the term of this patent is extended or adjusted under 35 U.S.C. 154(b) by 0 days.

(21) Appl. No.: 09/237,788

(22) Filed: Jan. 26, 1999

(51) Int. Cl.[7] ............................... G01N 1/26; G01N 1/22
(52) U.S. Cl. .................. 73/23.2; 73/23.31; 73/863.82
(58) Field of Search .................. 73/23.2, 23.31, 73/863.82

(56) References Cited

U.S. PATENT DOCUMENTS

| | | |
|---|---|---|
| 4,526,028 * | 7/1985 | Hubner ................................. 73/23.2 |
| 4,561,288 | 12/1985 | Moenkhaus ....................... 73/23.31 |
| 4,607,963 * | 8/1986 | Ulrickson ............................. 374/131 |
| 4,786,472 | 11/1988 | McConnell et al. . |
| 5,206,818 | 4/1993 | Speranza ................................ 73/23.2 |
| 5,415,025 | 5/1995 | Bartman et al. . |
| 5,479,359 | 12/1995 | Rogero et al. ......................... 422/83 |
| 5,526,280 | 6/1996 | Consadori et al. . |
| 5,970,781 * | 10/1999 | Hiss, III et al. .................. 73/863.82 |
| 6,095,682 * | 8/2000 | Hollander et al. .................... 374/121 |

* cited by examiner

Primary Examiner—Daniel S. Larkin
(74) Attorney, Agent, or Firm—Young & Basile, P.C.

(57) ABSTRACT

A method and apparatus for monitoring stack gas emissions wherein a probe including temperature and pressure indicating transducers is sequentially located at predetermined positions within a smokestack and the output of such transducers is fed into an electronic data logger for retention therein. The data logger includes a light hand held module having a liquid crystal display and start/reverse/advance pushbutton switches whereby the data logger can be remotely controlled. The invention eliminates the necessity of using two operators to record the desired information and significantly reduces the cost of producing accurate evaluation of stack gas emissions.

4 Claims, 1 Drawing Sheet

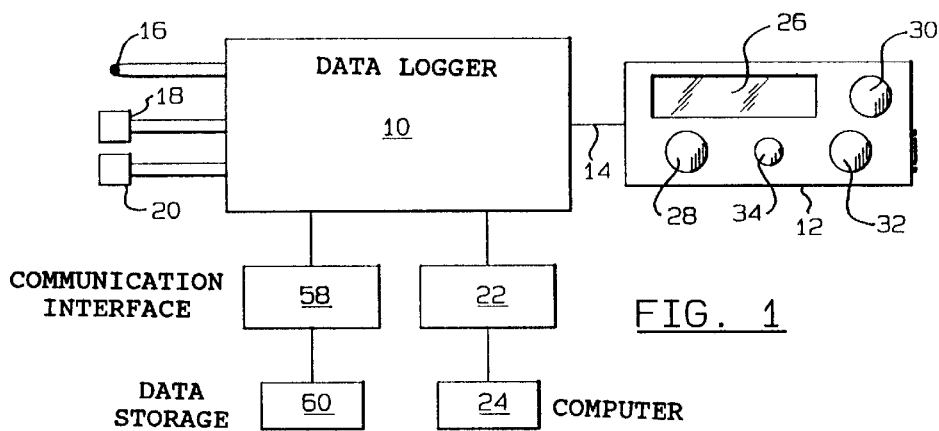
FIG. 1
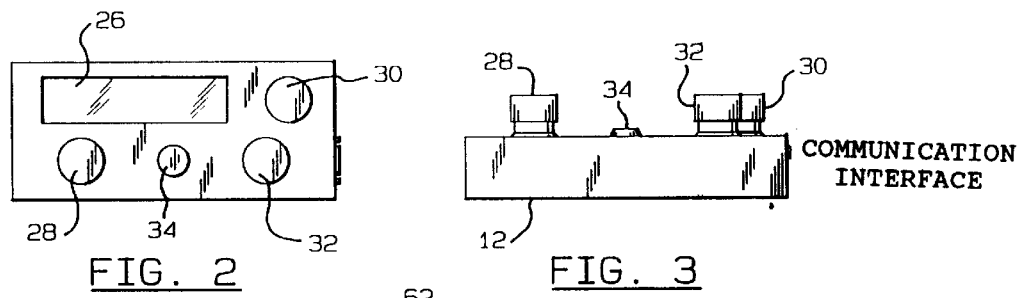
FIG. 2    FIG. 3
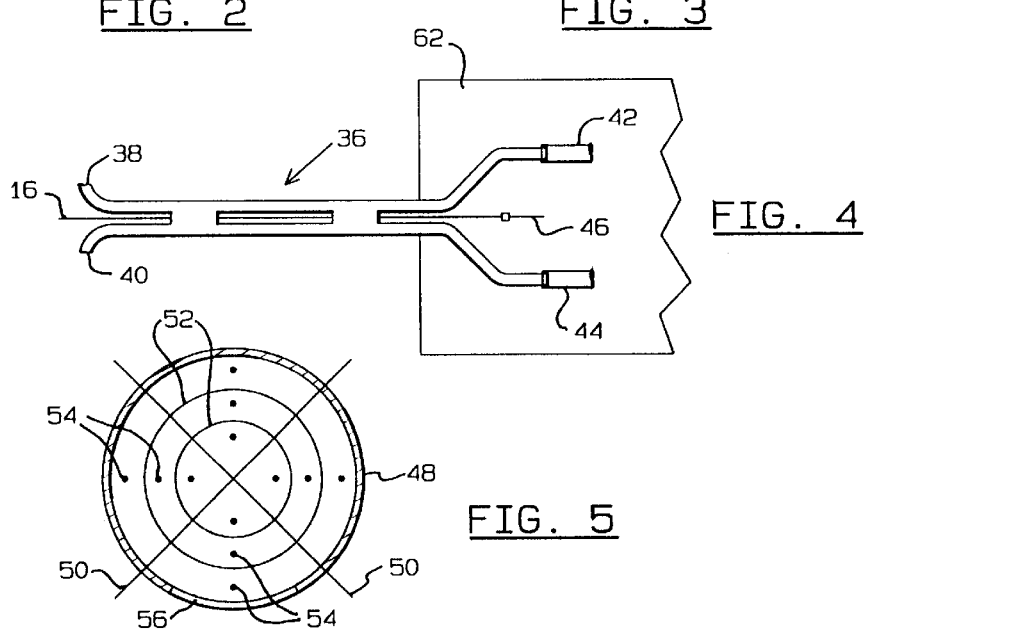
FIG. 4
FIG. 5

STACK GAS EMISSIONS MONITORING SYSTEM

BACKGROUND OF THE INVENTION

1. Field of the Invention

The invention pertains to stack gas emissions monitoring systems using moveable gas differential pressure and temperature measurement devices whose readings are electronically recorded for analysis.

2. Description of the Related Art

Environmental standards require that gaseous emissions from smokestacks, particularly large stacks such as used by utility companies in the generation of electric power, meet predetermined emission standards. Periodic testing of the gaseous stack emissions is required and conducted, and reports are regularly submitted to the appropriate government environmental agencies.

In the past, gaseous stack emissions were determined by locating differential pressure and temperature measurement devices temporarily within the smokestack at predetermined locations, and the measurements were manually recorded. Such recording was accomplished by one individual placing the measurement devices into the flue gas stream within the smokestack, and another individual nearby recording the readings from analog instruments connected to the output of the measurement devices.

Usually, the stack gases are monitored at more than one horizontal location within the smokestack, and several ports, or openings in the stack wall to facilitate such measurements, are arranged along a horizontal plane around the circumference of the smokestack. This traditional system of flue gas flow measurement is expensive and time consuming (requiring two operators), and is subject to errors in the reading of the analog meters, data recording at the test location, and subsequent data transcription to computer spreadsheets for the final calculations and report.

A variety of sophisticated electronic systems and devices have been utilized in the analysis of emissions from various sources, and such devices are illustrated in U.S. Pat. Nos. 4,561,288, 4,786,472, 5,206,818, 5,415,025, 5,479,359, and 5,526,280. However, devices such as shown in these patents are not specifically designed for the measurement of volumetric flow of stack gas emissions.

OBJECTS OF THE INVENTION

It is an object of the invention to provide a method and apparatus for economically measuring the volumetric flow of flue gas emissions wherein such measurements require only a single operator and accurate readings are assured.

A further object of the invention is to provide a system for measuring volumetric flow of flue gas emissions which may be readily used by a technician with minimal training, is concise in its size and easily handled under difficult conditions and in cramped quarters, and wherein the readings of the measurement system are accurately recorded and stored for analysis purposes.

SUMMARY OF THE INVENTION

In the practice of the invention, an electronic data logger records the output of a temperature sensing thermocouple, and a pair of differential pressure transducers. The output of these transducers into the data logger is controlled by a remote control device hardwired to the data logger and operated by the same person that operates the probe on which the measurement devices are located. When the probe is properly positioned in the flue gas stream within the smokestack, a "read" pushbutton is actuated by the operator to read, and then store the output values of the transducers at that time. The operator will sequentially locate the probe at predetermined locations within the smokestack so that the data logger can measure and record temperature and differential pressures at the predetermined number of locations in the cross sectional area of the flue gas flow. In this manner, variations in the flue gas flow due to turbulence, wall friction, and the like, can be determined.

The remote control module also includes pushbuttons to "reverse" and "advance" the data logger measurement point, whereby the past measurement points can be remeasured if thought to be in error, and the data logger can then be advanced to the next position at which readings are to be taken.

In order to be assured that the data logger has received all of the necessary information at each position within the smokestack, a dual-colored red/green LED is located on the remote control device, and will display a green light if the correct measurements have been recorded. Conversely, if there is an error in the measurement due to unintelligible or spurious readings, the LED will display a red light, and the operator can then remeasure at that location. The remote control device also is equipped with a back lighted LCD, which displays the numerical location of the current measurement point, and the value of the temperature and differential pressure measurements.

The electronic data logger may be directly connected to a personal computer (PC), or may be connected to an electronic data storing device for later input into a PC. The data logger software installed on the PC allows the user to view and evaluate the readings taken within the smokestack. The apparatus used in the practice of the invention is conventional equipment commercially available, and the practice of the invention significantly improves the accuracy, speed and cost of flue gas volumetric flow measurement methods currently in use.

BRIEF DESCRIPTION OF THE DRAWINGS

The aforementioned objects and advantages of the invention will be appreciated from the following description and accompanying drawings wherein:

FIG. 1 is a schematic view of the apparatus used in the practice of the invention for the measurement of volumetric flow of stack gases, FIG. 2 is a plan view of the remote control module, FIG. 3 is a side elevation view of the remote control module, FIG. 4 is an elevation view of a typical probe for insertion into the stack gas stream and to which the differential pressure transducers and thermocouple type temperature measurement devices are connected, and FIG. 5 is a typical cross sectional view of a smokestack in which emission testing takes place, illustrating the positions of testing to achieve uniformity of testing across the gas flow.

DESCRIPTION OF THE PREFERRED EMBODIMENTS

With reference to FIG. 1, the apparatus of the invention includes an electronic data logger 10 which is capable of receiving electronic signals from temperature and differential pressure transducers and storing such signals. The data logger 10 may be of conventional construction such as sold by Campbell Scientific, Inc. Model CR10X.

The data logger 10 is connected to a remote control module 12 by hard wire 14, and the wire 14 may be of a length of as much as fifty feet or more so that the data logger 10 may be securely supported on a firm surface in an environmentally friendly area, while the module 12 will be hand carried by the operator. If desired, the module 12 could include a wireless transmitter sending signals to a wireless receiver associated with data logger 10.

Temperature and pressure transducers are connected to the data logger 10 providing the input signals thereto. A thermocouple 16, FIG. 1, is connected to the data logger, and a pair of differential pressure transducers 18 and 20 also provide an electronic input into the data logger. The thermocouple 16 is of the type "E" while differential pressure transducer 18 is of the Omega PX655 series having a range of zero to one inch of water, and the differential pressure transducer 20 is also of the PX655 series having a measurement range between zero and twenty-five inches of water.

An electronic communications interface 22 such as made by Campbell Scientific, Inc. Model SC32A, may also be connected to the data logger 10 and the interface 22 may be connected to a personal computer (PC) 24. A different communications interface 58 such as made by Campbell Scientific, Inc. Model SC532 may be connected to the data logger 10, and then may be connected to a data storage module 60 such as made by Campbell Scientific, Inc. Model SM192.

The remote control module 12 is of a size as to be easily carried by the operator, and includes a Liquid Crystal Display (LCD) 26, a "read" pushbutton switch 28, a "go forward" pushbutton switch 30, a "go back" pushbutton switch 32, and an indicator 34 of the Light Emitting Diode (LED) type that may selectively glow red or green. The operation of the components of the remote control module 12 are described below.

The thermocouple 16 is mounted intermediate the arms 38 and 40 of a S-type pitot tube 36, which in turn is affixed to a probe 62. The thermocouple 16 is electrically connected to the data logger 10 by wire 46. The differential pressure transducers 18 and 20 are mounted in a box along side the data logger 10. The differential pressure transducers 18 and 20 are connected to the S-type pitot tube 36 by rubber tubing 42 and 44. The probe 62 is usually of a rigid pipe design, but may take other forms. Both differential pressure transducers 18 and 20 are connected in parallel across the arms 38 and 40 of the S-type pitot tube 36. The electronic output of the differential pressure transducers 18 and 20 are hardwired directly to the data logger 10.

In FIG. 5, a cross section of a typical smokestack is illustrated. The method and apparatus of the invention is often practiced in very large smokestacks such as found in power plants, wherein the exhaust gases from fuel combustion to produce steam for electric generation passes through the smokestack 48. The smokestack 48, in a horizontal plane, has been divided into quadrants by imaginary lines 50 and imaginary circles 52 concentric to the stack axis locate the test points 54 which are the points at which testing of the stack gases are made. The test points 54 radially extend from the center of the stack 48 outwardly close to the stack walls, and the test points at equal locations from the center of the stack are each spaced in a different quadrant. In this manner, a fair representation of the characteristics of the gas within the stack 48 is made, and such readings will be relatively free of variations due to turbulence, stack wall friction, and other gas flow affecting characteristics.

In operation, the operator locates the data logger 10 on a firm supporting surface, and usually, the stack port 56 defined in the stack will be remote with respect to the location of the data logger. The operator will open the test port 56 and holds the probe 62 in his hand. As the S-type pitot tube 36 is connected through the inside of the probe 62 to the data logger 10 by flexible rubber tubing 42 and 44 and the thermocouple 16 is connected through the inside of the probe 62 to the data logger 10 by flexible wire 46, the probe may be moved and located within the stack 48 as desired. The outer end of the S-type pitot tube 36 and thermocouple 16 will be positioned at one of the test points 54. Thereupon, the operator will push the "read" pushbutton switch 28 wherein the output of the differential pressure transducers 18 and 20 and the thermocouple 16 will be recorded in the data logger 10. The operator will then move the probe 62 to a different test point 54 and again push the "read" pushbutton switch 28 to record the temperature and differential pressure of the flue gas stream at that point. This procedure is repeated until all of the test point locations 54 reachable through the test port 56 have been measured. The operator will then carry the probe 62 to the next test port 56 and repeat the process. These steps will be repeated until all test point locations 54 within the stack 48 have been measured.

Each time the "read" switch 28 is actuated, the LED indicator 34 will glow either red or green. If the indicator is green, the data logger 10 has received sufficient and correct information from the differential pressure transducers 18 and 20 and from the thermocouple 16, and the data logger 10 will advance its internal counter to the next measurement point. If the output of the thermocouple 16 or the pressure transducers 18 and 20 is incomplete, or outside a set of preprogrammed parameters, the signals will be considered in error, and the LED indicator 34 will glow red, and the operator will have to again push the "read" pushbutton 28 until the LED 34 glows green to indicate correct readings have been achieved.

If the operator desires to remeasure a previous point for any reason, the "go back" pushbutton switch 32 is actuated until the LCD 26 shows the proper numerical location for the test point 54 the operator wishes to remeasure. The "read" pushbutton 28 must be pushed until the LED indicator 34 glows green. The operator must then simultaneously push the "go back" pushbutton 32 and the "go forward" pushbutton 30 until the LCD 26 displays the proper numerical location for the next test point 54 to be measured.

Once the testing has been completed, the information stored within data logger 10 may be transferred directly to a PC 24, via the communications interface 22. Alternately, the information stored within the data logger 10 may be transferred to a data storage module 60 via communications interface 58, and the data storage module 60 is then used as the input to the PC 24. Either method of recovering the information stored within the data logger 10 allows the operator to view and evaluate the test results, and to permit printing of the test results.

From the above description, it will be appreciated that accurate monitoring of volumetric gas flow in a smokestack may be quickly and easily completed by a single operator, the accuracy of the readings are improved, and all operator error in the recording and transfer of test measurements is eliminated, and as each reading is checked for its completeness, a high degree of accuracy is achieved. The operator may proceed at his own desired rate of testing, and the apparatus of the invention provides many advantages over prior arrangements for measuring volumetric flow of flue gas emissions.

It is appreciated that various modifications to the inventive concepts may be apparent to those skilled in the art without departing from the spirit and scope of the invention.

What is claimed is:

1. A stack gas emissions monitoring system process for measuring volumetric gas flow using an electronic data logger, a remote control electronically connected to the data logger controlling the operation thereof, a probe having first and second gas pressure sensing electronic transducers each having an output connected to the data logger, and an electronic temperature sensing transducer having an output connected to the data logger; the remote control including an electronic display panel and a "read" switch to record the transducers' output in the data logger, comprising the steps of: positioning the probe at a predetermined position within a vertical stack having gas flowing upwardly therein; closing the read switch on the remote control to store the probe values within the data logger; repositioning the probe within the stack at the same vertical elevation as the previous reading; closing the read switch to store the probe values within the data logger; repositioning the probe within the stack to other predetermined positions within the stack at the same vertical elevation and storing the probe output at each position within the data logger; and transferring the stored data from the data logger to an evaluation apparatus for measuring volumetric gas flow, the remote control including a forward switch, a reverse switch, and first and second indicator lights; the forward switch advancing the data logger to the next gas sensing position and the reverse switch returning the display to the last position reading.

2. In a stack gas emission monitoring system process as in claim 1, including the step of sensing the reading taken at a predetermined location to determine if the reading meets a predetermined standard and indicating acceptability of such reading with said indicator lights.

3. A stack gas emission monitoring system for measuring volumetric gas flow comprising, in combination: an electronic data logger, a remote control electronically connected to the data logger controlling the operation thereof, a probe having first and second gas pressure sensing electronic transducers each having an output connected to said data logger, an electronic temperature sensing transducer having an output connected to said data logger; an electronic evaluation and computer device connected to said data logger to evaluate the data thereof to measure volumetric gas flow; said remote control including an electronic display panel and a "read" switch to record said transducers' output to said data logger; the remote control including a forward switch, a reverse switch, and first and second indicator lights; said forward switch advancing the data logger to the next gas sensing position and said reverse switch returning the display to the last position reading, said probe being insertable into a gas emissions stack to take a reading of the gas temperature and pressure at a predetermined location.

4. In a stack gas emission monitoring system as in claim 3, data storage means connected to said data logger whereby information signals stored in said data logger may be transferred to said data storage means.

* * * * *